United States Patent [19]

Rhenter et al.

[11] Patent Number: 4,878,916
[45] Date of Patent: Nov. 7, 1989

[54] PROSTHETIC CUPULE

[75] Inventors: Jean-Luc Rhenter, 11, rue de l'Annonciade, 69001 Lyon; Jean Collomb, L'Olagnier, 26800 Portes-Les-Valence, both of France

[73] Assignees: Jean-Luc Rhenter; Jean Collomb; Jacques Bejui, all of France

[21] Appl. No.: 300,173

[22] Filed: Jan. 19, 1989

Related U.S. Application Data

[63] Continuation of Ser No. 124,946, filed as PCT FR87/00064 on Mar. 10, 1987, published as WO87/05490 on Sep. 24, 1987, abandoned.

[51] Int. Cl.⁴ .............................................. A61F 2/34
[52] U.S. Cl. .......................................... 623/18; 623/22
[58] Field of Search ..................... 623/16, 18, 20, 21, 623/22, 23

[56] References Cited

U.S. PATENT DOCUMENTS

| 4,695,282 | 9/1987 | Forte et al. ........................... 623/22 |
| 4,704,127 | 11/1987 | Averill et al. ......................... 623/18 |
| 4,715,860 | 12/1987 | Amstutz et al. ....................... 623/22 |

FOREIGN PATENT DOCUMENTS

| 0091315 | 4/1983 | European Pat. Off. ............. 623/22 |
| 0139356 | 7/1984 | European Pat. Off. ............. 623/22 |
| 2297030 | 6/1976 | France ................................. 623/22 |
| 2493139 | 6/1980 | France ................................. 623/22 |

*Primary Examiner*—Richard J. Apley
*Assistant Examiner*—David J. Isabella
*Attorney, Agent, or Firm*—Arnold, White & Durkee

[57] ABSTRACT

Prosthetic cupule comprising:
  a metallic support cupule (6),
  a friction cupule in plastic material (20), of which the external shape corresponds to the internal shape of the support cupule,
characterized in that:
  the support cupule (6) is provided in its center with an opening (14);
  the external shape of the friction cupule (20) comprises respectively a first cylindrical portion (22), joining up with a truncated portion (23), which is itself joined with a flat portion (25) provided in its center with a cylindrical central lug (24);
  and in that the internal face (21) of the friction cupule (6) is semi-spherical.

9 Claims, 2 Drawing Sheets

PROSTHETIC CUPULE

This is a continuation of application Ser. No. 124,946 filed as PCT FR87/00064 on Mar. 10, 1987, published as WO87/05490 on Sep. 24, 1987, now abandoned.

The invention relates to a new type of prosthetic cupule.

It is known that a prosthesis is essentially composed of two parts, namely respectively, on the one hand, a pin designed to be inserted in the bone, provided at its other end with a head over which is hingedly mounted the cupule which is itself engaged in another bone of the articulation.

Mostly, heretofore, the cupule is produced in two separate parts, which are:

a cupule known as a "support cupule", designed to be inserted in one of the bones of the articulation to be reinforced or replaced;

and the other part known as "friction cupule" designed to be inserted in the support cupule and to receive the head of the prosthetic pin engaged in another bone of the same articulation.

Mostly, the support or external cupule is normally produced in metal, such as titanium or titanium alloy, whereas the internal friction cupule is produced in plastic material, such as polyethylene (see for example Pat. Nos. FR-A-2 297 030, 2 493 139 or European Pat. Nos. 0091315 and 0139356).

Assembly between the external cupule and the internal cupule is mostly achieved either by screwed joint, or by way of a holding fillet, or by using male and female parts designed to be inserted one into the other during a rotation.

Briefly, all the dispositions used up to now imply internal cupules of complex shapes, hence expensive, and require fitting operations that are rather delicate and demand an accurate positioning of the articulation.

In the aforecited Pat. No. FR-A-2 493 139, the described prosthesis is of the type in which the swivel, which is of spherical shape and designed to fit in the pelvis is filled with polyethylene. A bore is cut in this damping filling for introducing a sleeve. During the fitting-in of the prosthesis, the surgeon then engages the sleeve which is locked in position in the bore on the conical end of the pin. When the temperature rises up to the temperature of the human body, the polyethylene expands to ensure a firm grip on the sleeve which is in turn gripped by morse fitting on the end of the pin. The assembly is thus firmly locked. This solution in which the friction in effect occurs between the bone and the metallic swivel presents nevertheless the following disadvantages:

on the one hand, it can only be adapted on protheses fitted in a sound pelvis, since the spherical shaped swivel is inserted in the bone without being fastened to it, on the other hand, with time, the damping filling in polyethylene which is friction-free, can become dislocated inside the swivel, which then induces intraprosthetic luxations.

The invention eliminates these disadvantages. It relates to a prosthesis of the type comprising two cupules, one for support and one for friction, respectively, which is easy and inexpensive to produce and in particular easy to fit and to remove.

Such prosthetic cupule composed of two parts, namely:

a metallic support cupule, designed to be fixed by a screwed joint in a bone of the articulation to be reinforced or replaced, a friction cupule in plastic material, designed to be inserted in the support cupule and to receive the spherical head of the prosthetic pin engaged in another bone of that same articulation, and in which the external shape of the friction cupule and the internal shape of the support cupule are complementary and fit closely together, characterized in that:

the metallic support cupule is provided in its center with a cylindrical through opening;

the external shape of the friction cupule, which is complementary to the internal shape of the support cupule, comprises:

at its base, a first cylindrical portion, joining up with a truncated portion, which is itself joined to a flat portion, and then to a central lug adopting the shape of the cylindrical through opening of the support cupule;

and in that the internal face of the friction cupule is semispherical in order to fit over the spherical head of the pin.

Advantageously, in practice :

the coefficient of expansion of the plastic material which constitutes the friction cupule is, at 20° C., at least twenty times greater than that of the metal constituting the support cupule;

the clamping between these two respective support and friction cupules is, at 37° C,, a positive clamping comprised between 0.07 mm and 0.005 mm, in order to obtain the best connection; indeed, if the clamping is more, then a considerable cooling will be required during the fitting operation, whereas if it is less, the machining will involve enormous costs for no noticeable improvement;

except for some play, the external dimensions of the friction cupule and the internal dimensions of the support cupule coincide, at 0° C., so that the friction cupule can easily be stored in sterile conditions, for example in a refrigerator.

The way in which the invention can be carried out and the advantages resulting therefrom will be more readily understood from the following example of embodiment, given by way of indication and non-restrictively, with reference to the accompanying drawings.

Figure 1:
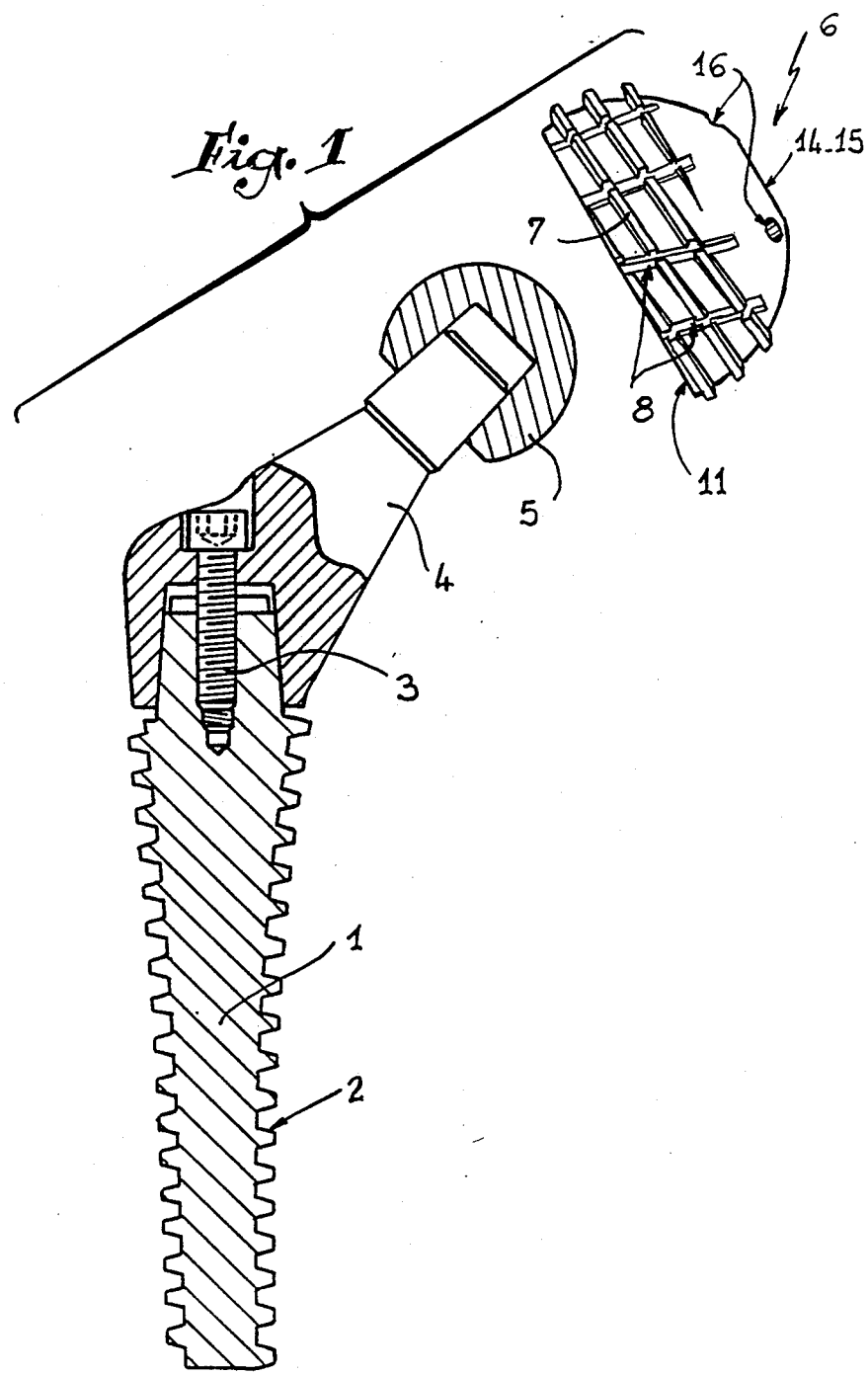
FIG. 1 illustrates a primary hip prosthesis.
Figure 2:
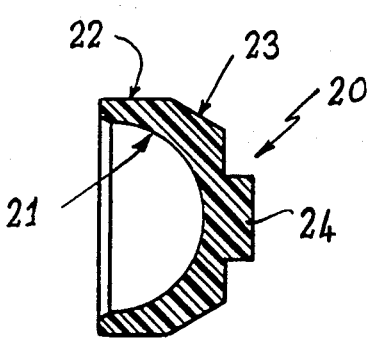
FIG. 2 illustrates a cross-section of a friction cupule according to the invention, designed to be inserted in a support cupule such as shown in cross-section in FIG. 3; the assembly being illustrated in FIG. 4.

As conventionally known, a hip prosthesis with primary fixation essentially comprises a femoral pin (1) threaded in (2) for insertion in the bone to be reinforced. Said pin (1) is joined via a screw (3) with a connecting piece (4) of which the end forms a head (5). Said head (5) is designed to cooperate with the cupule bearing the general reference (6) and equally threaded in (7) for insertion in another bone of the hip.

Figure 3:
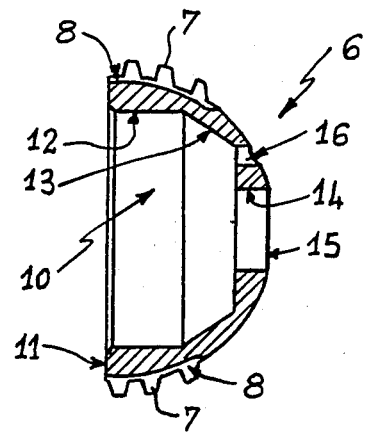
Figure 4:
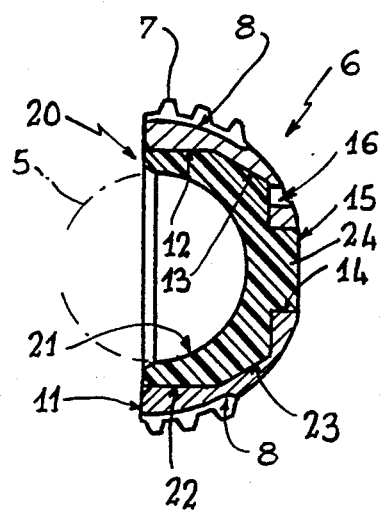
Figure 5:
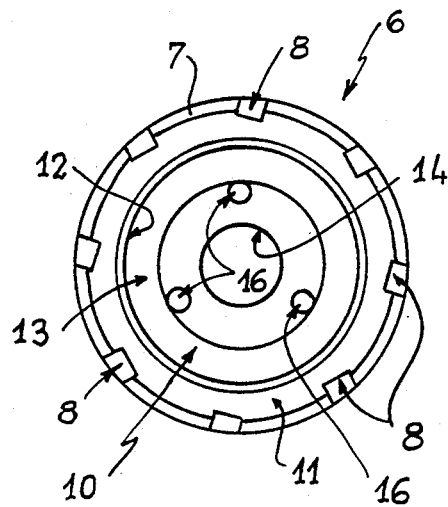
FIG. 5 illustrates the support cupule viewed from under its base.

In known manner, said cupule (6) illustrated in FIGS. 3 and 4 is threaded (7) and comprises self-cutting notches (8), eight in number for example. Said external support cupule (6) is produced in titanium or titanium alloy. The external face of said cupule is adapted to the bone which it is designed to reinforce. According to a characteristic of the invention, the internal face (10) of the support cupule comprises, starting from its base (11) a first cylindrical portion (12) joined up with a truncated portion (13), which latter is joined up to a cylindrical portion (14) emerging in (15). According to one advantageous embodiment designed to reinforce the acetabulum, the diameter of cylindrical portion (12) is forty millimeters (whereas the external diameter of the cupule (6) is fifty-six millimeters), the diameter of the cylindrical portion (14) is seventeen millimeters and the height of the assembly (12,13) is twenty millimeters, and finally the inclination of the truncated portion (13) is 30°.

The upper face of the cupule comprises three orifices (16), shifted angularly and intended for the screwed joint.

According to the invention, the friction cupule, designated by the general reference (20) and which is in high density polyethylene, such as for example of the RCH 1000 type, comprises firstly, a semi-cylindrical internal portion (21) designed to fit over the cotyloid pin (4). According to the characteristic of the invention, the external diameter of the friction cupule (20) also has a diameter of forty millimeters. The external face of said cupule (20) comprises firstly a first cylindrical portion (22) designed to fit over (12), which portion is joined up with a truncated portion (23) designed to be fitted in (13) and is ended by a horizontal plane (25) provided in its center with a lug (24) designed to be inserted in orifice (15) while resting against the walls (14).

As conventionally known, the coefficient of expansion of the titanium alloy forming the support cupule (6) is $8.5 \times 10^{-6}$ by degree at 20° C., whereas that of the polyethylene forming the friction cupule (2) is $210 \times 10^{-6}$ by degree at 20° C.

The external support cupule (6) can be stored at the atmospheric temperature.

The internal friction cupule (20), on the contrary, is advantageously kept in a refrigerator, hence in sterile conditions.

During the surgical operation, the support cupule (6) is fitted. Then, the internal friction cupule (20) is brought out of the refrigerator and impacted in (10). Under the effect of the temperature of the human body, the internal cupule (20) expands much quicker than the external cupule (6) and as a result sets itself inside of (10) molding itself to the walls of portions (12,13,14).

If by any chance, and for any reason whatsoever, the surgeon has to remove the cupule, he only needs to cool down the internal cupule (20) and the latter can withdraw itself automatically without any problem, this being done for example by applying a cold source on the face (21).

The implementation of the invention is characterized:

on the one hand, by the simplicity of design of the two cupules, which makes their machining an easy operation, resulting in a reduced cost;

by its fittability since it is no longer necessary for the internal and external cupules to be placed angularly in rotation.

The embodiment according to the invention differs from that of Pat. No. FR-A-2 493 139 described in the preamble, in that:

first of all it is perfectly adaptable on a worn and/or deformed pelvis;

it is easy to remove by a simple cooling operation on the spherical face (21);

there is no intraprosthetic luxation between the polyethylene cupule and the support cupule;

and finally, the support cupule (6) adheres firmly to the bone and once it is fitted, there is no rotation, so that a perfect locking is achieved;

contrary to the prior art, the polyethylene cupule fulfills a friction function;

finally, the two cupules are fitted in separately, this permitting ready replacement of either one, and in particular of the support cupule.

Thus, this type of cupule can find numerous applications in the field of prostheses necessitating the use of friction cupules, such as hip prostheses or knee prostheses, in short, any prostheses for the articulations.

We claim:

1. A prosthesis cupule, comprising:
a metallic support cupule for fixing to a bone, and a friction cupule of plastic material having an internal surface in the form of a concave approximate semi-sphere to fit over a spherical head of a pin, an axis of said semi-spherical surface being normal to the central plane defining the extent of the approximately semi-spherical surface, and an external surface comprising at least one surface parallel to said axis, the coefficient of expansion of the plastic material constituting the friction cupule is at 20° C. sufficiently greater than that of the metal constituting the support cupule, so that the expanded friction cupule is compressed and tightly held within the support cupule at body temperature, that is at about 37° C.,
said metallic support cupule having an internal cavity for receiving the external face of the friction cupule;
and wherein at body temperature, said friction cupule expands and is compressed against said internal cavity and tightly held therein, thereby providing the sole engagement between said friction and metallic support cupules.

2. A prosthesis cupule according to claim 1, wherein the friction cupule comprises a central lug portion adapted to fit in a traversing cylindrical portion provided in said metallic support, said axis of the semi-spherical surface of said friction cupule normal to the central plane defining the extent of the approximately semi-spherical surface passing through said lug, said lug having at least one surface parallel to said axis.

3. A prosthesis cupule according to claim 1, wherein the support cupule is titanium or titanium alloy and the friction cupule is high density polyethylene.

4. A prosthesis cupule according to claim 1, wherein the coefficient of expansion of the plastic material to the friction cupule is, at 20° C., at least twenty times higher than that of the metal of the support cupule.

5. A friction cupule according to claim 1, wherein the friction cupule is compressed by the support cupule in an amount in the range of about 0.005 to about 0.07 mm at body temperature.

6. A method of interconnecting a friction cupule and metallic support cupule to form a prosthesis cupule, comprising:
providing a friction cupule of plastic material having an internal surface in the form of a concave approximate semi-sphere to fit over a spherical head of a pin, an axis of said semi-spherical surface being normal to the central plane defining the extent of the approximately semi-spherical surface, and an external surface comprising at least one surface parallel to said axis;

a metallic support cupule, for fixing to a bone, said metallic cupule having an internal cavity for receiving the external face of the friction cupule, an internal shape of the cavity of the metallic support cupule being exactly complementary to the shape of the external face of the friction cupule at 0° C. so that said uncompressed friction cupule is freely rotatable within the metallic cupule, the coefficient of expansion of the plastic material constituting the friction cupule being, at 20° C., greater than that of the metal constituting the support cupule; and fitting the friction cupule with the metallic support cupule by cooling the friction cupule to a temperature such that the friction cupule is slidably received in the metallic support cupule, and allowing the temperature of the friction cupule to increase such that the friction cupule is securely held in the support cupule, thereby providing the sole engagement between said friction and metallic support cupules.

7. The method of claim 6, wherein the support cupule is titanium or titanium alloy and the friction cupule is high density polyethylene.

8. The method of claim 6, wherein the friction cupule is compressed an amount in the range of about 0.005 to about 0.07 mm at body temperature.

9. The method of claim 6, wherein the coefficient of expansion of the plastic material of the friction cupule is, at 20° C., at least twenty times higher than that of the metal of the support cupule.

* * * * *